United States Patent [19]  
Richer

[11] Patent Number: 4,877,619  
[45] Date of Patent: Oct. 31, 1989

[54] LIPOSOMAL VESICLES FOR INTRAPERITONEAL ADMINISTRATION OF THERAPEUTIC AGENTS

[75] Inventor: LeRoy L. Richer, San Gabriel, Calif.

[73] Assignee: Vestar, Inc., Pasadena, Calif.

[21] Appl. No.: 35,065

[22] Filed: Apr. 6, 1987

Related U.S. Application Data

[63] Continuation-in-part of Ser. No. 900,122, Aug. 25, 1986, abandoned.

[51] Int. Cl.$^4$ .................. A61K 37/22; A61K 9/66; B01J 13/02
[52] U.S. Cl. ................... 424/450; 264/4.1; 424/1.1; 428/402.2; 436/829
[58] Field of Search ............ 264/4.1; 428/402.2; 424/450, 1.1; 436/829

[56] References Cited

U.S. PATENT DOCUMENTS

| | | | |
|---|---|---|---|
| 4,309,421 | 1/1982 | Ghyczy et al. | 514/568 X |
| 4,522,803 | 6/1985 | Lenk et al. | 428/402.2 X |
| 4,619,795 | 10/1986 | Cohen | 428/402.2 X |
| 4,708,861 | 11/1987 | Popescu et al. | 264/4.1 X |

*Primary Examiner*—Richard D. Lovering  
*Attorney, Agent, or Firm*—Lyon & Lyon

[57] ABSTRACT

Liposomal multilamellar vesicles suitable for sustained delivery of therapeutic agents to the peritoneal cavity and a method for their formulation are described. The liposomal multilamellar vesicles comprise a phosphatidylcholine having fatty acid side chains of from 12 to 24 carbons in length and have a size of from about 1 micron to about 15 microns in diameter.

13 Claims, No Drawings

LIPOSOMAL VESICLES FOR INTRAPERITONEAL ADMINISTRATION OF THERAPEUTIC AGENTS

The present application is a continuation-in-part of U.S. patent application Ser. No. 900,122, filed Aug. 25, 1986, now abandoned.

BACKGROUND OF THE INVENTION

The mammalian peritoneal cavity drains into the circulatory blood system via two routes: splenic blood capillaries and the lymphatic system. Blood capillary drainage is believed to be primarily responsible for removal of lower molecular weight materials (below about 20,000 MW) from the peritoneal cavity, while the lymphatic system, which provides drainage through various lymph nodes and through the thoracic duct and other lymph ducts, is primarily responsible for removal of higher molecular weight (about 70,000 MW) materials. Experiments involving a number of therapeutic agents have demonstrated that the peritoneal cavity is cleared very rapidly of such agents when they are administered in their free chemical form. In such cases, the therapeutic agent is typically passed to the circulatory system and out of the body relatively quickly. Liposomal vesicles have been used to encapsulate various therapeutic agents, and it has been shown that such vesicles exhibit increased uptake by the liver and spleen upon intravenous injection, thus allowing targeting of encapsulated therapeutic agents to such organs.

Experiments in which liposomal vesicles have been injected into the peritoneal cavity have generally been directed toward increasing delivery of encapsulated agents to the lymphatic system. Thus, Ellens, et al., Biochim. Biophys. Acta, Vol. 674, pp. 10-18 (1981), determined that encapsulated $^{125}$I-labeled poly (vinyl pyrrolidone) in sphingomyelin and cholesterol was taken up by the liver and spleen after intraperitoneal injection at a rate reduced by a factor of 2-3 compared to intravenous injection. Although the peritoneal cavity appeared to act as a reservoir for vesicles for some hours following intraperitoneal injection, clearance of the $^{125}$I label from the peritoneum led to less than 5% of the total initial injected dose remaining in that cavity after 12 hours. A number of researchers have verified increased lymphatic uptake following intraperitoneal injection of liposomal vesicles. Thus, Rahman, et al., Eur. J. Cancer Clin. Oncol., Vol. 20, No. 8, pp. 1105-1112 (1984), used multilamellar vesicles formulated from dipalmitoylphosphatidylcholine, cholesterol and stearylamine to encapsulate radiolabeled antitumor agent 1-$\beta$-D-arabinofuranosylcytosine (ara-C) and determined that intraperitoneally-injected vesicles were more effective in treating mice lung tumors than intravenously-injected vesicles. This result was theorized to be attributable to sustained release of the ara-C, presumably due to an increased drug concentration in the lymphatics. Similarly, Hirano and Hunt, J. Pharm. Sci., Vol. 74, No. 9 (Sept. 1985), measured the biodistribution after intraperitoneal injection of small unilamellar vesicles and multilamellar vesicles (0.048-0.72 micron in diameter) composed of egg phosphatidylcholine, cholesterol, dipalmitoyl phosphatidic acid and alpha-tocopherol, and concluded that although absorption from the peritoneum to the lymphatics did not depend on vesicle size (more than about 50% of the injected radiolabel being absorbed from the peritoneum after 5 hours), retention within the lymphatics was dependent on size. The goal of this study was to increase lymphatic uptake as distinct from retaining the vesicles within the peritoneal cavity. Similar results were obtained by Parker et al., Cancer Res., Vol. 41, pp. 1311-1317 (April 1981), wherein adriamyci encapsulated in dipalmitoyl-phosphatidylcholine-cholesterolstearylamine vesicles (diameter less than 0.6 micron) were shown to be accumulated in the lymph nodes draining the peritoneal cavity.

Earlier work by Parker et al., Drug Metab. Dispos., Vol. 10, pp. 40-46 (1982) showed that liposomes composed of egg phosphatidylcholine, cholesterol, stearylamine and radiolabelled dipalmitoyl-phosphatidylcholine and used to encapsulate ara-C (size apparently less than 0.6 micron) exhibited increased lymphatic uptake after intraperitoneal injection compared to free ara-C, as well as 40-60% retention of radiolabelled material in peritoneal washings taken 6 hours after injection. Patel and Ryman noted in Knight (ed), Liposomes: From Physical Structure to Therapeutic Applications, Chapter 15, pp. 409-440 at 425 (Elsevier/North-Holland Biomedical Press 1981) that multilamellar vesicles too large to enter the lymphatics may act as a "depot" for intrapped drugs at the site of intraperitoneal injection. However, the later studies of Hirano and Hunt, discussed above, showed that MLV clearance from the peritoneal cavity appeared to be size independent for those vesicles studied (up to about 0.72 micron in diameter). Moreover, the extent of retention in the peritoneal cavity is not shown to be of any therapeutic significance.

U.S. Pat. No. 4,427,649, Dingle et al. (Jan. 24, 1984) proposes the use of compositions comprising anti-inflammatory steroid derivatives encapsulated in liposomes formed from dimyristoyl-, dipalmitoyl- or distearoylphosphatidylcholines (diameter greater than about 0.1-0.5 micron) to treat inflammatory conditions involving an enclosed cavity, as for example intra-articular joints. Although use within the peritoneum is proposed, this speculation is never tested and there is no indication that the problem of lymphatic drainage was even recognized in the intraperitoneal administration context. For example, it has been noted by Poste et al. in Gregoriadis (ed.), Liposome Technology, Volume III, chapter 1, pp. 2-26 at 20 (CRC Press, Inc. 1984) that the problem of sustaining liposomal residence in the peritoneal cavity is more difficult than in joints, where liposomes are known to persist for considerable times.

SUMMARY OF THE INVENTION

The present invention provides improved liposomal vesicles for delivery of therapeutic agents to the peritoneal cavity. In particular, these vesicles are capable of achieving sustained delivery of therapeutic agents to the peritoneal cavity compared to other delivery media, thus allowing lower dose administration and improve peritoneal targeting.

The delivery vesicles comprise a lipid component further comprising a phospholipid component selected from the phosphatidylcholines having fatty acid side chains of from 12 to 24 carbons in length, and most preferably 16 to 20 carbons in length. The diameter of the vesicles is from about 1 micron to about 15 microns or larger, with about 5 microns to about 15 microns being preferred. A preferred phosphatidylcholine is distearoylphosphatidylcholine. A non-phospholipid lipid component, preferably cholesterol, may be included in the vesicle lipid component, most preferably in a molar ratio of 2 to 0.5–1.5 (phospholipid to cholesterol). A therapeutic agent, as for example a non-steroidal anti-inflammatory drug such as ibuprofen or tolmetin, or an antimicrobial, antitumor, immunomodulatory or diagnostic agent, is incorporated into the liposomal vesicle and is delivered to the peritoneal cavity for a sustained period upon intraperitoneal administration.

In another aspect of the invention, methods for formulating the present liposomal vesiclesaare disclosed whereby maximal incorporation of the therapeutic agent into the vesicle is achieved by adjusting the relative amounts of lipid component and therapeutic agent with respect to selected hydration media.

Accordingly, the present invention provides improved vesicles for intraperitoneal delivery of therapeutic agents. In another aspect, it provides improved therapeutic preparation specially adopted for delivering agents useful for treating physiological conditions occurring within the peritoneum. Also provided are methods for preparing the vesicles and using them to achieve therapeutic results.

DETAILED DESCRIPTION

Studies undertaken with regard to the present invention have demonstrated that improved delivery of therapeutic agents to the peritoneal cavity is achieved using the intraperitoneal liposomal delivery vesicles described herein. These delivery vesicles exhibit extended retention time in the peritoneal cavity, resulting in increased delivery of therapeutic agent and prolonged therapeutic effect for a given dose of therapeutic agent. This allows medical treatment using smaller doses and/or less frequent administration of therapeutic agents while still retaining a beneficial level of therapeutic activity. In addition, the present invention provides a means for improving the targeting of therapeutic agents to the peritoneal cavity by reducing and/or delaying the transmission of such agents to other portions of the body (e.g., the lymphatic system). The invention thus provides for intraperitoneally localized, as opposed to systemic, drug delivery, and thus allows therapeutic treatment of physiological conditions occurring within the peritoneum, i.e., within the peritoneal cavity or in tissue proximate to the serous peritoneal membrane. In addition, the invention provides for sustained delivery of therapeutic agents to the peritoneal cavity and, to the extent transport to other portions of the body is desirable, sustained delivery of therapeutic agents to these other portions.

In particular, the utility of the present delivery vesicles in preventing and treating adhesions, a common postoperative complication frequently involving the peritoneum and, for example, bowel tissue, has been demonstrated where the therapeutic agent is a non-steroidal anti-inflammatory drug such as tolmetin or ibuprofen. Other applications, by way of example, may include sustained delivery of antimicrobial agents to the peritoneal cavity; sustained delivery of, for example, insulin or other drug agent to the peritoneal cavity during peritoneal dialysis procedures; and targeted delivery of antitumor agents to the peritoneal cavity during treatment of, for example, ovarian cancer. Examples of antimicrobial agents include, but are not limited to, aminoglycosides, such as amikacin, gentamicin, and tobramycin, and other agents such as methicillin and amphotericin B. Other agents which may benefit therapeutically by intraperitoneal release include immunomodulators such as interferon-gamma, muramyl-dipeptide and the interleukins. Antitumor agents would include cytotoxic antineoplastic agents such as doxorubicin and cisplatin. Diagnostic or imaging agents may also be used as therapeutic agents. Other uses for the delivery vesicles described herein will be apparent to those skilled in the medical arts.

A number of factors determine the successful intraperitoneal delivery of therapeutic agents using the present invention. First, the size of the intraperitoneal liposomal delivery vesicles ("ILDVs") will be in the range of approximately 1 micron to approximately 15 microns or longer in diameter. A preferred size range is from about 5 microns to about 15 microns in diameter. Such ILDVs correspond in size to what are known in the art as "multilamellar vesicles" ("MLVs"), which comprise roughly spherical liposomal structures having a multiplicity of phospholipid bilayers. In contrast, small unilamellar vesicles ("SUVs"), which are generally in the range of approximately 20 nm to approximately 100 nm (0.02 micron to 0.1 micron) in diameter, do not exhibit the prolonged intraperitoneal retention time of the present ILDVs. Large unilamellar vesicles ("LUVs"), which generally fall intermediate in size between SUVs and MLVs, do not normally exceed 1 micron in diameter and are therefore less readily used in the present invention.

A second important consideration in the practice of the present invention is the composition of the ILDV. It has been found that liposomal delivery vesicles having appropriate characteristics of size and composition will exhibit improved and prolonged intraperitoneal retention times that render such vesicles useful for intraperitoneal drug delivery. In particular, ILDVs comprising as their phospholipid component a phosphatidylcholine having fatty acid side chains of from 12 to 24 carbons in length are particularly suitable for use in the present invention. It is preferred that the fatty acid side chains in the phosphatidylcholine be saturated and of from 14 to 20 carbons in length, and most preferably 16 to 20 carbons in length. Illustrative preferred phosphatidylcholines are as follows (in which "PC" stands for "phosphatidylcholine"):

| Common Name | Systematic Name | Side Chain Carbons |
| --- | --- | --- |
| dilauroyl PC | di-n-dodecanoyl PC | 12 |
| dimyristoyl PC | di-n-tetradecanoyl PC | 14 |
| dipalmitoyl PC | di-n-hexadecanoyl PC | 16 |
| distearoyl PC | di-n-octadecanoyl PC | 18 |
| diarachidoyl PC | di-n-eicosanoyl PC | 20 |
| dilignoceroyl PC | di-n-tetracosanoyl PC | 24 |

One highly preferred phosphatidylcholine is distearoyl phosphatidylcholine ("DSPC"). It has been found that use of DSPC yields ILDVs which are particularly stable in the in vivo environment and which also exhibit particularly prolonged intraperitoneal retention times.

Furthermore, it is preferred that the phospholipid component of the ILDV be composed of a substantially pure form of the appropriate phospholipid. For example, "egg PC," which is a mixture of naturally-derived phosphatidylcholines of varying carbon side chain lengths, does not yield maximum intraperitoneal retention time or vesicle stability in ILDVs. It is thought that both intraperitoneal retention time and vesicle stability are highly dependent on the composition of the liposomal vesicle. For this reason, it is in many cases preferable to control the composition carefully, as for example by limiting the phospholipid component to a single, substantially pure phosphatidylcholine. Suitable purified phospholipids are available from, for example, Avanti Polar Lipids.

It is also preferable to include a cholesterol, a cholesterol ester or other non-phospholipid lipid component in the ILDV composition. Such components appear to assist in stabilizing the ILDVs in the physiological environment, and thereby preventing overrapid release of the contained therapeutic agent. As is noted in following discussions, the prolonged intraperitoneal retention time of a therapeutic agent is due to is incorporation into an ILDV, whereas a "free" therapeutic agent (i.e., one not incorporated in an ILDV or one administered alone into the peritoneum) is rapidly removed from the peritoneal cavity. Therefore, it is important to achieve an ILDV which is stable in the physiological environment in that it is not degraded too quickly and also does not "leak" its therapeutic agent too rapidly.

Cholesterol ("CHOL") is a highly preferred non-phospholipid lipid component in the ILDVs of the present invention. It has been found that a mixture of phosphatidylcholine and cholesterol in a PC:CHOL molar ratio of about 2:0.5–1.5 is particularly suitable. A PC : CHOL molar ratio of 2:1 is preferred, with DSPC : CHOL in a ratio of 2:1 being an especially preferred combination.

Preparation of phospholipid or phospholipid-cholesterol mixtures may be achieved using a number of methods known in the art. Sterile or aseptic methods are generally required if in vivo administration of the final ILDVs is contemplated. One acceptable method involves dissolving with agitation appropriate quantities of phospholipid (e.g., DSPC) and non-phospholipid components (e.g., cholesterol) in a suitable solvent such as chloroform. The resultant solution is then evaporated to dryness using gentle heating in a rotary vacuum evaporator. Sterility may be maintained by using a 0.22 micron Millex filter attached to the air intake of the evaporator and by placing a sterile septum on the mouth of the flask after evaporation. A thin lipid film coating the sides of the flask is obtained. The film is then flushed for about 30 minutes with nitrogen introduced to the flask through a filtered, sterile needle passed through the septum. The flask is then vacuum desiccated for about 12 hours to yield a dried, stable lipid film.

EXAMPLE 1

Preparation of Lipid Film

L-alpha-distearoyl phosphatidylcholine ("DSPC"), 1.21 g, and 0.29 g cholesterol (molar ratio of DSPC to cholesterol is 2:1) are dissolved in 45 ml of chloroform. The resulting solution is divided into nine 5 ml portions, and each such portion is placed in a 100 ml flask. The solvent is evaporated from the flask using a rotary vacuum evaporator. Sterility is maintained by attaching a 0.22 micron Millex filter to the air intake of the evaporator prior to flask removal. Sterile septa are placed on the flasks after solvent evaporation. The surface of each septum is wiped with 70% alcohol, and a 19 gauge sterile needle affixed to a 0.22 micron filter is passed through each septum. All flasks are then placed in a large vacuum desiccator and kept there overnight. Each flask contains about 167 mg of lipid.

Alternately, the phospholipid component may be prepared by spray drying. Phospholipid or phospholipid and cholesterol are dissolved in a suitable solvent, such as chloroform, with heat and agitation to a minimum concentration of approximately 30% (w/v). The lipid is then spray dried to a fine powder in a spray drying apparatus using an air-nitrogen mixture. Example operating conditions include an air temperature of 71° C., air input of 3.5–4.5 m$^3$/min, a nozzle setting of 1.5–2.0 kg/cm$^2$ and a feed rate of 5–8 ml/min.

A therapeutic agent may be incorporated into a liposomal delivery vesicle of the present invention by hydration with an appropriate lipid component in a suitable solvent. Hydration should also be carried out in a sterile or aseptic manner. It is generally carried out with agitation, as for example using vortex stirring (small flask-size samples) or a tissue/solution homogenizer (larger samples). It has been found that either of the above agitation techniques yield ILDVs with very similar drug encapsulation efficiency and in vivo efficacy. The hydration mixture should be heated to a temperature which approaches the phase transition temperature of the lipid component; 65° C. is a suitable temperature for a 2:1 DSPC:CHOL lipid mixture. Hydration in a laboratory scale sample may be completed in approximately one hour, while longer periods of up to about 24 hours may be required for large-scale mixtures. The step may be carried out under a filtered nitrogen flow. In the case of spray-drying, it has been demonstrated that the spray dry and hydration protocol can be scaled up to produce large quantities of ILDVs. By this method batches of 1–30 L volumes have been produced, and much larger volumes are attainable using the same methodology.

EXAMPLE 2

Preparation of ILDVs from Lipid Film

The sodium salt of ibuprofen (Na-IBF), 0.202 gm is dissolved in 40 ml of sterile, pyrogen-free water. The solution is then passed through a 0.22 micron Millex filter.

3.9 ml of the Na-IBF solution is injected into each flask containing lipid film. The flasks are vortex-stirred for 40 to 60 minutes in a 65° C. water bath under nitrogen. (The nitrogen purge is first passed through a 0.22 micron filter.) To the contents of each flask is added sterile, pyrogen-free phosphate buffered saline, and the flasks are centrifuged for 6 to 10 minutes at 15,000 rpm. This washing procedure is repeated for a total of five times to remove unencapsulated Na-IBF. The contents of the flasks are then combined and PBS (5 mM PO$_4^{3-}$ in 0.15 N NaCl) is added to a total of 32 ml. The liposome suspension thus produced comprises ILDVs of about 1 micron or larger in size suspended in the PBS. It is storage-stable for a period of several months, but for long term storage is preferably dehydrated and remixed with sterile, pyrogen-free water just before use.

To prepare drug-free controls, the above procedure is carried out substituting pure water for the water/Na-IBF solution.

The procedure is repeated using (a) the free-acid form of IBF, and (b) the sodium salt of tolmetin. Similar results are obtained and ILDVs containing IBF or sodium tolmetin are produced.

Analogous procedures would be employed to produce vesicles from phosphatidylcholines in which the fatty acid moieties were derived from other fatty acids, e.g., $C_{12}$ to $C_{24}$ fatty acids. $C_{14}$ to $C_{20}$ saturated fatty acids are preferred.

The formulation of ILDVs having maximal incorporation of therapeutic agent and proper liposomal structure, size and stability generally requires proper attention to a number of considerations. These include the choice of a suitable hydrating solvent, use of proper relative amounts of lipid and therapeutic agent and use of a suitable hydration solution volume.

Choice of a suitable hydration solvent involves the ability of the solvent to dissolve or suspend a suitable quantity of therapeutic agent as well as the ability to allow formation of ILDVs having the proper characteristics and therapeutic agent content. It is sometimes desirable to modify the therapeutic agent chemically in order to render it suitably soluble or more stably incorporated into an ILDV, as for example by converting the therapeutic agent to a salt form. In the case of the non-steroidal anti-inflammatory drugs ibuprofen and tolmetin, conversion to the sodium salt from the free acid form of each drug was found to markedly enhance incorporation of the drugs into ILDVs. This effect is thought to be due to the detergent-like behavior of the free acid forms, which acts at higher concentrations to prevent proper vesicle formation. In other cases, it may be necessary to modify the therapeutic agent chemically in order to achieve a solubilized concentration high enough to allow sufficient incorporation into the ILDV. Nevertheless, ILDVs from the free acid form of, for example, ibuprofen have been produced using the methods of the present invention and shown to be of therapeutic benefit.

A variety of solvents or solvent systems may be used in the hydration step. With the therapeutic agents sodium ibuprofenate and sodium tolmetinate, it has been found that sterile water is a preferred solvent for phosphatidylcholinecholesterol lipid mixtures. Two-phase solvent systems, which use immiscible polar and nonpolar solvents, may also be usefully employed depending on the relative polar and nonpolar solubilities of the ILDV components.

Although it is generally preferable to maximize the amount of therapeutic agent incorporated into an ILDV, it is not desirable in every case to maximize the solubilized concentration of the therapeutic agent in the hydration mixture. Rather, optimum results in terms of drug incorporation and vesicle characteristics generally require a balancing of solvent ionic strength, therapeutic agent concentration and lipid concentration. As noted above, the optimum solvent for the therapeutic agents sodium ibuprofenate and sodium tolmetinate in a DSPC-CHOL vesicle is sterile water. Alternate solutions of varying ionic strength, although capable of dissolving these agents and the lipid component, yield lower drug encapsulation.

EXAMPLE 3

Effect of Hydration Solvent on ILDV Formation

Table 1 shows the effect of varying hydration solvents with respect to formation of sodium ibuprofenate ILDVs. ILDVs were formed using the methods described in Example 2, and may also be formed using the homogenizer agitation method discussed above. Drug incorporation in Table 1 was ascertained using HPLC analysis.

TABLE 1

Entrapment of Sodium Ibuprofenate in Various Hydrating Media (Lipid = DSPC:CHOL, 2:1)

| Lipid (mg) | Hydrating Medium (vol) | Sodium Ibuprofenate (mg) | % Encapsulated |
|---|---|---|---|
| 40 | 70 mM $PO_4^{3-}$ (2 ml) | 2.0 | 1.05 |
| 40 | 70 mM $PO_4^{3-}$ (2 ml) | 8.0 | 2.70 |
| 40 | $H_2O$ (1 ml) | 10.0 | 5.07 |
| 40 | $H_2O$ (1 ml) | 5.0 | 25.08 |
| 40 | 2.5 mM $PO_4^{3-}$ (1 ml) | 5.0 | 8.86 |
| 40 | PBS (2 ml) | 8.0 | 13.05 |

As seen in Table 1, an optimum encapsulation of sodium ibuprofenate is achieved using 40 mg/ml DSPC:CHOL lipid (2:1) in a water hydration solution containing about 5.0 mg/ml sodium ibuprofenate. A range of from about 3.0 mg/ml to about 8.0 mg/ml sodium ibuprofenate is preferred. A similar lipid concentration, i.e., 40 mg/ml, was found to be suitable for formation of sodium tolmetinate ILDVs.

EXAMPLE 4

Effect of Lipid and Drug Concentrations on ILDV Formation

Table 2 shows the results of aqueous entrapment of sodium ibuprofenate in a water hydration solution for various lipid compositions and drug concentrations. The effect of high concentrations of therapeutic agent in preventing vesicle formation is clearly seen here, as is the superiority of the DSPC-cholesterol lipid mixture as the encapsulating material. A net incorporation of about 1 mg sodium ibuprofenate or greater per 35 mg of vesicle lipid per ml of solution may routinely be achieved using the methods of the present invention.

TABLE 2

Aqueous Entrapment of Sodium Ibuprofenate (Varying Concentrations and Lipid Mixtures)

| Lipid (40 mg) (Composition) | Sodium Ibuprofenate (mg) | Solution Volume (ml) | % Encapsulated |
|---|---|---|---|
| DSPC:CHOL (2:1) | 35.9 | 2.0 | 0.15 |
| DSPC:CHOL (2:1) | 18.0 | 1.0 | 0.24 |
| DSPC:CHOL (2:1) | 9.0 | 1.0 | 7.84 |
| DSPC:CHOL (2:1) | 4.5 | 1.0 | 20.34 |
| DSPC:CHOL (2:1) | 4.5 | 1.0 | 16.93* |
| DPPC:DSPC:CHOL (6:2:1) | 18.0 | 1.0 | 0.31 |

*This trial carried out in water followed by six rinses of ILDVs with phosphate-buffered saline (PBS); other trials carried out in water followed by six rinses of ILDVs with water.

EXAMPLE 5

Formation of Sodium Tolmetinate ILDVs

Table 3 shows aqueous entrapment of sodium tolmetinate in DSPC:CHOL (2:1) vesicles. Hydration was carried out in water for one hour at 65° C. with vortex stirring, following by six washings of the ILDVs in PBS. Encapsulation was measured by HPLC or $^{14}$C-tolmetin measurement.

TABLE 3

Aqueous Entrapment of Sodium Tolmetinate (Lipid = DSPC:CHOL, 2:1)

| Lipid (mg) | Sodium Tolmetinate (mg) | Solution Volume (ml) | % Encapsulated |
| --- | --- | --- | --- |
| 40 | 15 | 1.0 | 35.6 |
| 40 | 15.7 | 1.0 | 19.3 |
| 40 | 15 | 1.0 | 21.5* |
| 40 | 10 | 1.0 | 27.5 |
| 40 | 10 | 1.0 | 33.3* |

*$^{14}$C—tolmetin analysis used.

As seen in Table 3, a concentration of 10-15 mg/ml sodium tolmetinate in water with 40 mg/ml DSPC:CHOL (2:1) lipid is a suitable hydration mixture. Higher concentrations of sodium tolmetinate, up to for example 30 mg/ml, have also been shown to be useful in scaled-up preparation. A net incorporation of about 2-3 mg sodium tolmetinate or greater per 35 mg of vesicle lipid per ml of solution may routinely be achieved using the methods of the present invention. As is the case with the sodium ibuprofenate vesicles discussed above, these therapeutically-useful levels of incorporation are maintained using scaled-up preparation methods as for example in 50-100 ml batch sizes. Appropriate concentrations of various components to form ILDVs for different therapeutic agents and different lipid components may be ascertained using routine experimentation under the procedures disclosed herein.

The hydration procedure described above results in the formation of ILDVs. It may be useful to blend the vesicle solution in a high speed blade homogenizer for several minutes after hydration to achieve homogeneity. Purification may be achieved by washing the obtained vesicles with sterile water or PBS, centrifuging the mixture at approximately 30,000 G for 6-10 minutes, and decanting the supernatant. This step is repeated 5 to 7 times. Large scale purification ma be achieved using ultrafiltration dialysis, where vesicles in buffer or other solvent are pumped past an ultrafilter membrane under pressure to remove lower molecular weight components, including unincorporated therapeutic agent.

The obtained ILDVs will have a size generally falling within the range 1-15 microns in diameter, and will have an MLV structure. The vesicles may be further purified as to size by resuspending them in PBS and passing them through several microfilters of varying size. A suitable storage solution may contain approximately 35 mg/ml vesicle in buffer, with an incorporated therapeutic agent content of 1-5 mg/ml or more. In the case of the sodium ibuprofenate and sodium tolmetinate vesicles prepared as described above using DSPC:CHOL (2:1), the vesicle size was typically about 10 microns in diameter. This remained true for both small (1 ml) and larger (e.g., 50-100 ml) preparation batches.

Following purification, the ILDVs may be stored as a suspension in PBS, or may be dried to a stable powder. One or more sterilization steps, as for example steam sterilization or autoclaving, may be performed prior to storage depending on the stability of the incorporated active ingredient and the particular vesicle formulation.

Tests performed with ILDVs of the present invention have shown the vesicles to have prolonged intraperitoneal retention and drug delivery times as well as measurable therapeutic benefit. As noted above, prior work in the field has shown that liposomal vesicles of a variety of sizes and compositions are rapidly removed from the peritoneal cavity with substantial uptake by various elements of the lymphatic system. The present ILDVs, however, are capable of delivering therapeutic agents to the peritoneal cavity for periods surpassing those heretofore known in the art.

EXAMPLE 6

Biodistribution of Free Radiolabel After Intraperitoneal Administration

In vivo biodistribution tests in rats using the gamma-emitting radionuclide Indium-III chelated to ethylenediamine tetracetic acid ($^{111}$In-EDTA) have shown that free $^{111}$In-EDTA administered intraperitoneally is rapidly excreted. In studies relating to the present invention, rats were injected intraperitoneally with $^{111}$In-EDTA at time zero and the uptake of the radionuclide in various tissues and samples measured after sacrifice at various times thereafter. Table 4 shows uptake values for these samples. At the times indicated in the table, the animals were anesthetized, exsanguinated and the peritoneal cavities lavaged three time with 20 ml phosphate-buffered saline. The lavage fluid was pooled and centrifuged at low speed. "Peritoneal fluid" refers to fluid lavaged and pooled from the peritoneal cavity and contains small sized vesicles. "Peritoneal pellet" refers to the pelleted portion of the lavaged peritoneal fluid, and contains cellular matter (predominately peritoneal macrophage) and large vesicles. The remaining tissues were collected, washed, blotted, weighed and distributed into tubes for gamma counting. All data reflects the average for three rats of the percent of total injected $^{111}$In-EDTA recovered in each sample material after sacrifice of the rats at the times indicated.

TABLE 4

$^{111}$In-EDTA Biodistribution, Free Injection (10 uCi/1.5 ml)

| | 1 hr. % Inj. Dose | 2 hrs. % Inj. Dose | 6 hrs. % Inj. Dose | 24 hrs. % Inj. Dose |
| --- | --- | --- | --- | --- |
| Blood | 2.4 | .209 | .148 | .1 |
| Liver | .44 | .140 | .122 | .1 |
| Spleen | .02 | .008 | .008 | .006 |
| Kidney | 1.67 | .780 | .55 | .4 |
| Stomach | .119 | .038 | .033 | .008 |
| Sm. Int. | 1.424 | .48 | .626 | .1 |
| Lg. Int. | .141 | .780 | 1.849 | 2.3 |
| Peritoneal Fluid | 2.757 | .306 | .007 | .015 |
| Peritoneal Pellet | .011 | .005 | .007 | .004 |
| Urine | 19 | 73 | 60.2 | 14.05 |
| Feces | 4.6 | .02 | 7.6 | 16.83 |
| TOTAL | 32.58 | 76.73 | 71.27 | 33.91 |

As indicated in Table 4, intraperitoneal injection of $^{111}$In-EDTA results in rapid clearance from the peritoneal cavity and from the whole body. Examination of $^{111}$In-EDTA levels in liver, kidney and excretia suggest that absorption and lymphatic transport may be mechanisms for elimination.

EXAMPLE 7

Biodistribution of Radiolabeled ILDVs After Intraperitoneal Administration

Tables 5 and 6 show data comparable to that of Example 6 for rats injected with $^{111}$In-EDTA incorporated into ILDVs composed of DSPC:CHOL (2:1). As seen therein, approximately 60% of the injected $^{111}$In-EDTA was recovered from the peritoneal cavity after 6 hours, with about 10% still recoverable after 120 hours. In addition, the liver and kidney values are approximately 3-5 times lower then those obtained after intravenous injection of the same material.

TABLE 5

$^{111}$In-EDTA Biodistribution, DSPC:CHOL Vesicle (3.83 uCi, 20.57 mg lipid/rat)

|  | 1 hr. % Inj. Dose | 3 hrs. % Inj. Dose | 6 hrs. % Inj. Dose | 8 hrs. % Inj. Dose |
|---|---|---|---|---|
| Blood | .523 | .448 | .11 | .145 |
| Liver | .576 | 2.27 | 3.415 | 6.33 |
| Spleen | .036 | .753 | .433 | 1.84 |
| Kidney | .284 | .147 | .118 | .145 |
| Stomach | .203 | .023 | .259 | .343 |
| Sm. Int. | .261 | 1.116 | .182 | .514 |
| Lg. Int. | .053 | .139 | 1.02 | 1.27 |
| Peritoneal Fluid | 12.29 | 11.05 | 11.18 | 1.43 |
| Peritoneal Pellet | 40.66 | 56.29 | 51.67 | 44.58 |
| Urine | 2.317 | 7.01 | 9.15 | 6.328 |
| Feces | 2.49 | 2.722 | 3.92 | .14 |
| TOTAL | 56.69 | 82.28 | 81.45 | 62.93 |

TABLE 6

$^{111}$In-EDTA Biodistribution, DSPC:CHOL Vesicles (3.622 uCi, 20 mg lipid/rat)

|  | 3 hrs. % Inj Dose | 24 hrs. % Inj Dose | 48 hrs. % Inj. Dose | 72 hrs. % Inj. Dose | 120 hrs. % Inj. Dose |
|---|---|---|---|---|---|
| Blood | .278 | .056 | .03 | .055 | .03 |
| Liver | 1.659 | 6.69 | 7.94 | 9.2 | 5.36 |
| Spleen | .197 | 1.44 | .775 | 2.33 | 1.21 |
| Kidney | .223 | .147 | .126 | .142 | .149 |
| Stomach | .069 | 4.25 | .838 | 1.26 | .801 |
| Sm. Int. | .32 | .191 | .229 | .925 | 1.146 |
| Lg. Int. | .053 | .792 | .259 | .209 | .508 |
| Peritoneal Fluid | 14.2 | 3.4 | 1.143 | .268 | 2.41 |
| Peritoneal Pellet | 42.37 | 34.6 | 22.73 | 12.53 | 7.48 |
| Urine | 5.72 | 16.6 | 22.43 | 30.84 |  |
| Feces | 2.24 |  |  |  |  |
| TOTAL | 67.39 | 64.34 | 56.50 | 57.76 |  |

In the study shown in Table 6, the peritoneal pellet was counted for $^{111}$In-EDTA, an aliquot counted for total cell content and the total cell suspension then plated in culture. After three hours in culture, the cells were washed and counted for adherent cells (macrophage), and the adherent cells then collected and counted for $^{111}$In-EDTA. Approximately 90-95% of the total cell population was adherent cells. However, the percent of injected dose recovered from adherent cells ranged only from 0.03% to 0.5% of injected dose. Therefore, the $^{111}$In-EDTA recovered at the indicated time points represented residual intact intraperitoneal ILDVs.

Experiments performed using radiolabeled ibuprofen and tolmetin indicate that the ILDVs of the present invention are effective in delivering active ingredients to the peritoneal cavity with a prolonged residence time. In addition, treatment of rabbits administered with intraperitoneally-administered ILDVs containing ibuprofen, sodium ibuprofenate and sodium tolmetinate demonstrated therapeutic utility of the ILDVs in preventing or reducing the development of surgical adhesions following surgically-induced tissue trauma.

EXAMPLE 8

Biodistribution of Radiolabelled Ibuprofen After Intraperitoneal Administration of ILDVs Table 7 shows the biodistribution of $^3$H-ibuprofen ILDVs after intraperitoneal injection into rats as described above with respect to $^{111}$In-EDTA vesicle biodistribution. $^3$H-ibuprofen was obtained from New England Nuclear. Vesicles were prepared in aqueous lipid hydration medium followed by homogenization and centrifugation/resuspension (six times). Radioactivity was measured by scintillation counting. Two lavage rinses were employed, first water (three times) and then PBS with 10% Triton X-100 to dislodge any remaining vesicles or drug potentially sticking to tissue. The collected lavage fluid was centrifuged and the pellet, containing cells and residual vesicles, and the supernatant, containing free drug, were counted in a scintillation counter. Liver, spleen and kidney were also collected, minced, digested with Protosol and counted for radioactivity.

TABLE 7

$^3$H—Ibuprofen Biodistribution, DSPC:CHOL Vesicles (557,660 dpm, 37 mg lipid/rat)

|  | 3 hrs. % Inj. Dose | 5 hrs. % Inj. Dose | 24 hrs. % Inj Dose |
|---|---|---|---|
| Blood | 2.54 | 1.27 | .37 |
| Liver | 6.83 | 8.67 | 11.7 |
| Spleen | .40 | 2.48 | 1.96 |
| Kidney | .60 | .44 | .37 |
| Lavage Fluid Triton X-100 | 11.1 | 6.25 | 1.15 |
| Lavage Fluid | 1.44 | 1.32 | 1.17 |
| Peritoneal Pellet | 27.0 | 19.65 | 5.04 |
| Total Peritoneum | 39.55 | 27.22 | 7.36 |
| Urine | 10.45 | 13.89 | 38.02 |
| Feces | 2.92 | 7.79 | 21.45 |
| TOTAL | 63.29 | 61.76 | 81.27 |

Note: Vesicles were formed with DSPC:CHOL in 2:1 ratio; two rats per time point. In one 24 hour injection, 12.7% of the injected dose was found to be subcutaneous. The 12.7% was subtracted from the original dose when calculating "% Injected Dose" for this time point.

Although the biodistribution of $^3$H-ibuprofen to the peritoneal samples is seen in Table 7 to be lower than that for $^{111}$In-EDTA in Tables 5 and 6, the measured values nevertheless indicate a pronounced increase in peritoneal delivery and residence time as compared, for example, to injected free $^{111}$In-EDTA (Table 4). On a percent injected dose basis, the apparent amounts of drug found in liver, spleen and kidney are 40-50% lower than the amount of injected dose typically observed from intravenously injected vesicle formulations.

The ability of the present ILDVs to achieve sustained delivery of a therapeutic agent to the peritoneal cavity may be measured in terms of the percent of injected dose of therapeutic agent remaining within the peritoneum after a given time following initial injection. As seen from Table 7, and as used herein, sustained delivery is evidenced by at least about 5% of the initial injected dose of therapeutic agent remaining within the peritoneum after 24 hours.

Moreover, the therapeutic utility of intraperitoneally-administered ibuprofen and tolmetin ILDVs has been shown to be superior to that of other delivery vehicles. In this regard, the disclosure of copending patent application Ser. No. 900,122 for "Method of Inhibiting Post-Surgical Adhesion Formation by the Topical Administration of Non-Steroidal Anti-Inflammatory Drug," filed Aug. 25, 1986, and now abandoned, by G. S. diZerega, D. B. Johns, S. W. Shalaby, W. D. Sheffield and L. L. Richer, is incorporated herein by reference.

Adhesion formation is a major post-surgical complication with no practical solution. The incidence of adhesion formation following surgery approaches 100 percent, according to some sources, with a clinically significant complication rate of about 5 to 10 percent, depending on the type of surgery. Among such complications are bowel obstruction, infertility, and pain. Occasionally, adhesions necessitate a second operative procedure to remove the adhesion, which may in turn further aggravate the problem.

On the basis of the results of animal studies and limited human clinical studies, the systemic administration of non-steroidal anti-inflammatory agents such as ibuprofen (usually in combination with other medicaments such as antibiotics) appears to be the most efficacious pharmacological means now known to reduce the incidence of post-surgical adhesions. An objection to this means is that relatively large amounts of the drug must be administered over a period of several days, thereby subjecting the patient to the significant risk of experiencing adverse side effects. Also, this means has been shown to be effective only in a limited number of types of surgical procedures, e.g., gynecological surgery. Systemic administration of ibuprofen to combat adhesions is generally regarded as requiring in excess of 20 mg ibuprofen/kg/day over the course of several days' treatment, often including pre-surgical treatment. Dosages as low as 2.5 mg/kg/day have been recommended by Singer in U.S. Pat. No. 4,346,108.

In addition to ibuprofen and its pharmaceutical acceptable salts or esters, other non-steroidal anti-inflammatory drugs such as tolmetin, indomethacin, sulindac, suprofen, oxyphenbutazone and pharmaceutically acceptable salts or esters thereof may be employed in treating adhesions or other inflammation-related disorders. As mentioned above, ibuprofen, sodium ibuprofenate and sodium tolmetinate have been shown to be particularly useful in preventing adhesions when administered intraperitoneally in the ILDVs of the present invention. For example, a total dose of about 0.15 mg/kg of ibuprofen in ILDVs of the present invention was found to be virtually completely effective in preventing formation of adhesions in rabbits challenged with abrasions (about 15 cm$^2$) to adjacent sites on the peritoneal side wall and large bowel. Similarly, a total dose of about 7.3 mg/kg of tolmetin resulted in only scant adhesion formation in rabbits challenged with the severe trauma of uteral horn abrasion. These results equaled or surpassed those obtained upon intraperitoneal administration of, for example, ibuprofen contained in poly (lactide-co-glycolide [65:35]) microcapsules, mini-pump administered ibuprofen, suprofen, sodium suprofenate or sodium tolmetinate in PBS, aqueous sodium tolmetinate, and tolmetin combined with varying concentrations of the ethoxylated sorbitan monooleate "Tween 80."

EXAMPLE 9

Adhesion Prevention Using Intraperitoneally Administered ILDVs

Tables 8 and 10 show the results of adhesion prevention experiments in rabbits using the ILDVs of the present invention. In these tables, New Zealand white female rabbits (1.8–2.0 kg) underwent midline laparotomy using acelepromazine and ketamine anaesthesia. A 3×5 centimeter abrasion was produced over the right-lateral peritoneal side-wall by scraping the surface peritoneum with a scalpel until punctate bleeding developed over the entire 3×5 centimeter area. A second abrasion covering the same total area (15 cm$^2$) using the same technique was developed 1.5–2.0 centimeters inferior to the initial site along the left-lateral peritoneal side-wall. This second site was used as an untreated control. The serosal surface of the large bowel adjacent to the peritoneal abrasion sites was also similarly abraded.

Seven days after the day of abrasion, the rabbits were sacrificed by pentobarbital overdose. The extent of adhesions was evaluated as follows:
1. No adhesions.
2. Filmy adhesions (separable).
3. Mild adhesions (not separable—covering up to about 35% of the test area).
4. Moderate adhesions (not separable—covering about 35 to 60% of the test area).
5. Severe adhesions (not separable—covering greater than about 60% of the test area).

The ILDVs used in this example were composed of DSPC:CHOL (2:1) prepared in a manner analogous to that described above. The treatment mixture consisted of 31 milliliters containing 1200 milligrams of ILDV and 35 milligrams of the free acid form of ibuprofen, suspended in 5 mM phosphate buffered saline. The vehicle control had the same composition, except that the ibuprofen was omitted. Each rabbit received 10 ml of suspension, which amounted to 3.5 mg of ibuprofen per rabbit. The treatment and vehicle control suspensions were dripped directly on the traumatized sites. Six rabbits received the liposome/ibuprofen treatment on the right side-wall site with the other site being untreated, and six rabbits received a vehicle control treatment (i.e., liposome without ibuprofen on the right side-wall site with no treatment on the other site. The rabbits were sacrificed 7 days post-operatively, and evaluated as described above. The results are displayed below in Table 8.

TABLE 8

| | Ibuprofen Adhesion Prevention Results | | |
|---|---|---|---|
| Rabbit No. | Ibuprofen | Treated Site | Untreated Site |
| 1 | yes | 1 | 1 |
| 2 | yes | 1 | 1 |
| 3 | yes | 1 | 4 |
| 4 | yes | 1 | 1 |
| 5 | yes | 1 | 1 |
| 6 | yes | 1 | 4 |
| 7 | no | 2 | 4 |
| 8 | no | 5 | 5 |
| 9 | no | 1 | 5 |
| 10 | no | 5 | 4 |
| 11 | no | 3 | 4 |
| 12 | no | 1 | 1 |

In the experiments reported above in Table 8, the rabbits receiving treatment by the ibuprofen/liposome combination were virtually free of adhesions, even on the sides that received no direct application of medicament. This is considered to be indicative of the fact that the medicament can migrate in the peritoneal cavity as a result of circulation of peritoneal fluid. Also, by gross observation, no tissue reaction or granulomas were found at the treated sites.

Table 10 shows the results of an adhesion prevention experiment similar to the foregoing wherein ILDVs (DSPC:CHOL, 2:1) containing sodium ibuprofenate were administered in conjunction with varying proportions of control MLVs containing no drug. The control MLVs (MLV-1 and MLV-2) and sodium ibuprofenate ILDVs were prepared using the ingredient proportions given in Table 9.

TABLE 9

|  | Hydration Volume (ml) | Lipid (mg/ml) | Total Lipid (mg) | Drug (mg/ml) | Drug/Lipid (by weight) |
|---|---|---|---|---|---|
| MLV-1 | 50 | 33 | 1675 | 0 | 0 |
| MLV-2 | 50 | 34 | 1710 | 0 | 0 |
| Na-Ibuprofenate ILDV | 50 | 33 | 1675 | 0.98 (49 g) | 0.029 |

In Table 10, the proportions of drug-containing and control vesicles that were mixed together and administered to test rabbits in the manner described above are shown, along with the results of evaluations of the rabbits seven days post-operatively.

TABLE 10

Sodium Ibuprofenate Adhesion Prevention Results

| Rabbit No. | Na-Ibuprofenate ILDV (ml) | Control MLV (ml) | EVALUATION Treated Site | Untreated Site |
|---|---|---|---|---|
| 1 | 10 | 0 | 1 | 1 |
| 2 | 10 | 0 | 3 | 3 |
| 3 | 10 | 0 | 1 | 1 |
| 4 | 3 | 7 | 1 | 4 |
| 5 | 3 | 7 | 1 | 4 |
| 6 | 3 | 7 | 1 | 5 |
| 7 | 3 | 7 | 1 | 4 |
| 8 | 1 | 9 | 1 | 1 |
| 9 | 1 | 9 | 1 | 1 |
| 10 | 1 | 9 | 1 | 1 |
| 11 | 1 | 9 | 1 | 1 |
| 12 | 0.3 | 9.7 | 1 | 3 |
| 13 | 0.3 | 9.7 | 1 | 3 |
| 14 | 0 | 10 | 4 | 5 |
| 15 | 0 | 10 | 5 | 3 |
| 16 | 0 | 10 | 3 | 3 |
| 17 | 0 | 10 | 4 | 5 |
| 18 | 0 | 10 | 3 | 3 |

The minimum effective dose of ILDV in the above adhesion experiments was apparently not approached. However, it is noted from Table 10, Rabbits 12 and 13, that a total dose of about 0.3 mg of sodium ibuprofenate in an ILDV carrier was effective. This equals about 0.15 mg/kg or 0.02 mg/cm$^2$ of abraded tissue area. A reasonable extrapolation of the data shows that a minimum effective concentration of a non-steroidal anti-inflammatory drug preparation applied in a single dose for adhesion prevention would be between about 0.025 mg and 5 mg of active drug agent per ml of applied ILDV solution. Appropriate ILDV dosages in these or other applications may be ascertained using routine experimentation well within the routine skill in the art.

EXAMPLE 10

Adhesion Prevention in Uterine Horn Model

In another series of adhesion prevention experiments, the uterine horn of New Zealand white female rabbits was used as the model for adhesion development. It is believed that the trauma induced in this type of surgical procedure is more apt to produce severe adhesions than any trauma ordinarily associated with surgery, and therefore this is a very severe test for evaluating the efficacy of a medicament in inhibiting the formation of post-surgical adhesions.

The rabbits were anesthetized using acelepromazine and ketamine, and then underwent a lower median laparotomy incision. The serosal surface of both uterine horns were then abraded by grasping them with a gauze surgical sponge and pulling them away from the uterus until punctate bleeding developed.

Immediately after the uterine horns were traumatized as described above, varying quantities of DSPC:CHOL (2:1) ILDVs containing sodium tolmetinate (prepared by a procedure analogous to that described above and suspended in PBS at a concentration of 40 mg ILDV and 1.46 mg sodium tolmetinate per ml of suspension) were dripped on the traumatized site, and the rabbits were then closed. Seven days post-operatively, the rabbits were sacrificed and the development of adhesions were evaluated.

The results of the evaluation were as follows, with the quantities indicated being the volume of ILDV suspension dripped on the site of surgical trauma:

| 10 ml | Scant adhesion |
|---|---|
| 3 ml | Scant adhesion, but a few more than with the 10 ml dose. The adhesions were filmy. |
| 1 ml | Mild adhesions. |
| Control | (no medicament) - Severe adhesions; essentially unable to open the rabbit without tearing adhesions which developed between the uterus and the bowel and between the uterus and the anterior peritoneal wall. |

The above-described study was repeated several times with the tolmetin ILDVs with essentially the same results.

Although the mode of application of ILDVs in the above experiments involved direct dripping onto the abrade intraperitoneal abrasion site, it is clear that alternate modes of application, including in particular intraperitoneal injection, may also be employed. It is noted that natural migration of ILDVs within the peritoneal cavity, caused for example by peristaltic contraction of the intestines, was seen in experiments discussed above to result in therapeutic benefit at intraperitoneal sites other than the direct application site. In addition, other active therapeutic agents may be substituted for the non-steroidal anti-inflammatory agents discussed above to treat a variety of conditions, with appropriate dosage and administration modes being discernable through routine experimentation and/or routine skill in the art.

What is claimed:

1. A composition including liposomal multilamellar vesicles suitable for sustained delivery of a therapeutic agent to the peritoneal cavity, said multilamellar vesicles comprising a lipid component further comprising a phospholipid component selected from the group consisting of phosphatidylcholines having fatty acid side chains of from 12 to 24 carbons in length and a therapeutic agent incorporated into said vesicles, said vesicles having a size of from about 1 micron to about 15 microns in diameter.

2. The composition of claim 1 wherein said lipid component further comprises a non-phospholipid lipid component.

3. The composition of claim 2 wherein the molar ratio of said phospholipid component to said non-phospholipid lipid component if 2:0.5-1.5.

4. A composition including liposomal multilamellar vesicles suitable for sustained delivery of a therapeutic agent to the peritoneal cavity, said multilamellar vesicles comprising a phospholipid component comprising distearoylphosphatidylcholine, a cholesterol component, and a therapeutic agent incorporated into said vesicles, said vesicles having a size of from about 1 micron to about 15 microns in diameter.

5. The composition of claim 4 wherein the molar ratio of distearoylphosphatidylcholine to cholesterol is 2:0.5-1.5.

6. The composition of claim 5 wherein the molar ratio of distearoylphosphatidylcholine to cholesterol is approximately 2:1.

7. A pharmaceutical preparation suitable for sustained delivery of a therapeutic agent to the peritoneal cavity comprising liposomal multilamellar vesicles incorporating a therapeutic agent, said therapeutic agent being chosen for treatment of a physiological condition occurring within the peritoneum, and said multilamellar vesicles having a size of from about 1 micron to about 15 microns in diameter and comprising a phospholipid component selected from the group consisting of phosphatidylcholines having fatty acid side chains of from 12 to 24 carbons in length.

8. The pharmaceutical preparation of claim 7 wherein the amount of said therapeutic agent delivered to the peritoneal cavity is sustained at the level of at least about 5% of the total initial dose of therapeutic agent after a period of 24 hours after initial administration of the pharmaceutical preparation.

9. The pharmaceutical preparation of claim 7 wherein said liposomal vesicles further comprise a non-phospholipid lipid component, the molar ratio of said phospholipid component to said non-phospholipid lipid component being 2:0.5-1.5.

10. The pharmaceutical preparation of claim 9 wherein said phospholipid component is distearoylphosphatidylcholine, said non-phospholipid lipid component is cholesterol, and the molar ratio of distearoylphosphatidylcholine to cholesterol in said liposomal vesicle is approximately 2:1.

11. The composition or pharmaceutical preparation of any of claims 1, 4 or 7 wherein said therapeutic agent comprises an antitumor agent, an antimicrobial agent, an immunomodulatory agent or a diagnostic agent.

12. A method for formulating a composition including liposomal multilamellar vesicles suitable for sustained delivery of a therapeutic agent to the peritoneal cavity comprising (1) forming a lipid component comprising a phosphatidylcholine having saturated fatty acid side chains of from 16 to 20 carbons in length;

(2) combining an appropriate amount of said lipid component with an appropriate amount of said therapeutic agent in a suitable hydrating medium; and (3) forming liposomal multilamellar vesicles incorporating said therapeutic agent and having a size of from about 1 micron to about 15 microns in diameter;

the amounts of said lipid component and said therapeutic agent in step (2) being chosen so as to maximize incorporation of the therapeutic agent into the liposomal multilamellar vesicles upon performing step (3).

13. The method of claim 12 wherein said hydrating medium is water and wherein the amount of said lipid component in step (2) is about 40 mg/ml of hydrating medium.

* * * * *